US006845162B1

(12) United States Patent
Emborg et al.

(10) Patent No.: US 6,845,162 B1
(45) Date of Patent: Jan. 18, 2005

(54) DEVICE FOR ACTIVE SOUND CONTROL IN A SPACE

(75) Inventors: Urban Emborg, Ljungsbro (SE); Mats Gustavsson, Helsingborg (SE); Siv Leth, Arholma (SE); Fredrik Samuelsson, Borensberg (SE)

(73) Assignee: A2 Acoustics AB, Linkoping (SE)

( * ) Notice: Subject to any disclaimer, the term of this patent is extended or adjusted under 35 U.S.C. 154(b) by 297 days.

(21) Appl. No.: 10/148,445

(22) PCT Filed: Nov. 27, 2000

(86) PCT No.: PCT/SE00/02343

§ 371 (c)(1), (2), (4) Date: Sep. 17, 2002

(87) PCT Pub. No.: WO01/41123

PCT Pub. Date: Jun. 7, 2001

(30) Foreign Application Priority Data

Nov. 30, 1999 (SE) .......................................... 9904339

(51) Int. Cl.$^7$ ........................ A61F 11/06; G10K 11/16; H03B 29/00

(52) U.S. Cl. .................. 381/71.4; 381/71.9; 381/71.11

(58) Field of Search .............................. 381/71.1, 71.4, 381/71.8, 71.9, 71.12, 71.14; 708/322

(56) References Cited

U.S. PATENT DOCUMENTS

| | | | | | |
|---|---|---|---|---|---|
| 5,170,433 | A | | 12/1992 | Elliott et al. | 381/71.4 |
| 5,337,365 | A | * | 8/1994 | Hamabe et al. | 381/71.12 |
| 5,410,604 | A | | 4/1995 | Saito et al. | 381/71.4 |
| 5,416,844 | A | | 5/1995 | Nakaji et al. | 381/71.4 |
| 5,473,699 | A | * | 12/1995 | Tamamura et al. | 381/71.4 |
| 5,493,616 | A | | 2/1996 | Iidaka et al. | 381/71.4 |
| 5,499,302 | A | * | 3/1996 | Nagami et al. | 381/71.4 |
| 5,689,572 | A | * | 11/1997 | Ohki et al. | 381/71.3 |
| 5,692,052 | A | * | 11/1997 | Tanaka et al. | 381/71.9 |
| 5,745,580 | A | * | 4/1998 | Southward et al. | 381/71.1 |
| 5,758,311 | A | | 5/1998 | Tsuji et al. | 381/71.4 |
| 5,953,428 | A | * | 9/1999 | Silverberg et al. | 381/71.14 |
| 6,275,591 | B1 | * | 8/2001 | Hsueh et al. | 381/71.11 |

FOREIGN PATENT DOCUMENTS

| | | |
|---|---|---|
| JP | 7-261774 | 10/1995 |

* cited by examiner

*Primary Examiner*—Xu Mei
(74) *Attorney, Agent, or Firm*—Swidler Berlin Shereff Friedman, LLP

(57) ABSTRACT

The invention refers to a device for sound control in a space (2) with a sound field from at least one sound source (3). The device includes a pulse sensor (5), which provides a pulse signal from the sound source (3). Moreover, the device includes a number of sound influencing members (8) for reducing the sound field in the space (2) and a number of sound sensors (9), which sense the actual sound field in the space and provide an error signal. A control unit includes a signal supplied device (11, 12), which receives a pulse signal and supplies a first signal to an adaptive filter (15). The filter has a number of filter coefficients and generates a drive signal for each sound influencing member (8). The signals supply device also supplies second signals to a calculating member (24), which calculates the value of the filter coefficients by the second signals and the error signals for updating the adaptive filter (15). A detecting member detects phase and frequency of the pulse signal and a coefficient table provides two sets of coefficients for generating the second signals from detected phase and frequency of the pulse signal.

13 Claims, 1 Drawing Sheet

DEVICE FOR ACTIVE SOUND CONTROL IN A SPACE

THE BACKGROUND OF THE INVENTION AND PRIOR ART

The present invention refers to a device for active sound control in a space with a sound field from at least one sound source according the preamble of claim 1.

A typical such device includes at least one pulse sensor, which senses a non-acoustic pulse signal of the sound source, for instance an engine of a vehicle. Consequently, the pulse sensor provides a pulse signal with a frequency which varies with a state of operation of the engine, i.e. the rotation speed of the engine. The pulse signal may thus include a fundamental frequency, for instance a number of ignition pulses per second and overtones to this frequency. The pulse signal is supplied to a detecting member, which is arranged to detect phase θ and frequency f of the pulse signal t(n). The device also includes a number of sound influencing members, normally loudspeakers, which are arranged to reduce the sound field in said space, and a number sound sensors, normally microphones, which each is arranged to sense the actual sound field in said space and provide an error signal.

The core of the device is a control unit which includes a signal supply device that receives the pulse signal and supplies a first signal, substantially consisting of sinusoidal components, to an adaptive filter of the control unit, which has a number of filter coefficients and generates a drive signal for each loudspeaker from the first signal. The signal supply device also supplies a set of second signals, substantially sinusoidal components, to a calculating member, which calculates the value of the filter coefficients by means of the second signals and the error signal and updates the adaptive filter by the calculated filter coefficients.

Furthermore, the control unit includes a clock which defines the clock pulses determining when the filter coefficients are to be updated. This updating is performed according to the formula:

$$\underline{w}_k(n+1) = v\,\underline{w}_k(n) - \mu \sum_{m=1}^{M} e_m(n) x'_{km}(n)$$

wherein $x'_{km}(n)=x(n)S_{km}(n)$ where $w_k(n)$ is the filter coefficients for each k, i.e. each loudspeaker, v is the so called leakage factor, $\mu$ is the step length for the updating, $e_m(n)$ is the error signal, for each m, i.e. each microphone, x(n) is the first signal, $S_{km}(n)$ is the so called impulse response, i.e. the impulse which each loudspeaker provides in each microphone, $S_{km}(n)$ is the estimated impulse response and $x'_{km}(n)$ is the second signal or the filtrated first signal, i.e. the first signal has been filtrated by the estimated impulse response.

Such devices are well known today and described in public documents and patents, for instance in the book Active Noise Control Systems from 1996 by Sen M. Kuo and Dennis R. Morgan, and the U.S. Pat. No. 5,170,433.

The calculation of the second signal $x'_{km}(n)$, i.e. the filtering of the first signal by the impulse response, is a scalar multiplication, which is to be done for each combination of a microphone and a loudspeaker and for each clock pulse, and which requires a high calculating capacity of the device. This filtering may normally be performed by a part of the control software executed in real time.

SUMMARY OF THE INVENTION

The object of the present invention is to provide a device with a simplified calculating model. In particular, it is aimed at a device requiring less calculating capacity.

This object is obtained by the device initially defined, which is characterised in that the signal supply device includes at least one coefficient table, which is arranged to provide two sets of coefficients for generating said second signals $x'_{km}(n)$ from detected phase and frequency of the pulse signal t(n).

By means of such a coefficient table, it is possible to replace the extensive scalar multiplications by obtaining an approximate value of the second signals $x'_{km}(n)$ by means of the coefficients obtained by table reading. Such a generation of the second signal is very suitable when reducing sound of low frequency, for instance the type of sound generated in a motor vehicle. Such engine related sound, in addition, frequently has a relatively slow variation of the frequency. Moreover, the impulse responses for sound in the inner space in a motor vehicle are relatively short. Due to this fact the approximation of the second signals, obtained in the manner described, is good.

According to an advantageous embodiment of the invention, the signal supply device includes a first signal supply member, which is arranged to receive detected phase and frequency of the pulse signal t(n) and supply said first signal x(n) to the adaptive filter, and a second signal supply member, which is arranged to receive detected phase and frequency of the pulse signal t(n) and supply said second signals $x'_{km}(n)$ to the calculating member. Thereby, the second signal member may include said coefficient table and a precalculating member, which is arranged to calculate said second signals $x'_{km}(n)$ by means of a first set of said coefficients and an approximate value, which is related to detected phase and frequency of the pulse signal t(n).

Such an approximate value may be obtained from a sinus table.

Thereby, the signal supply device, either the first signal supply member or the second signal supply member, may include at least one approximate sinus table, which is arranged to provide said approximate value from a second set of said coefficients and detected phase and frequency of the pulse signal t(n). Such a sinus table may have a limited size, but preferably it offers an approximate value which is related to or is a satisfactory approximation of the first signal x(n).

According to a further embodiment of the invention, said first coefficients are related to the amplitudes ρ of said second signals $x'_{km}(n)$. Said second coefficients may include a set of delay coefficients θ', which define phase relations between the pulse signal t(n), possible the first signal x(n), and said second signals $x'_{km}(n)$. By using the actual value of the frequency and the phase position of the first signal, an approximate history of the first signal may be determined. Since the frequency of the first signal merely may take predetermined values, which are determined by the processing rate, it is possible to decide in advance which such approximate histories of the first signal can be present during operation.

Together with the estimation of the impulse responses $S_{km}(n)$, which can be assumed to be known and substantially invariant during operation, one may thus calculate and store good approximations of the results of a filtering of approximate histories of the first signal by the impulse response. In the device according to the invention, the previous, calculating-intensive, explicite filtering is reduced by a suitable approximate filtering result in the form of one or several amplitude and phase corrections for one or several harmonic components in the first signal. The second signal may thus be obtained by the formula $$x'_{km}(n)=\rho_{km}(f)\text{table}(n-\theta'_{km}(f)).$$

According to a further embodiment of the invention, the first signal supply member includes at least one table, which is arranged to provide the first signal x(n) from detected phase and frequency of the pulse signal t(n). This table of the first signal supply member includes said approximate sinus table. The number M of sound sensors are at least equal to the number K of sound influencing members.

According to a further embodiment of the invention, the control unit includes a clock, which defines a processing rate $f_s$, wherein the control unit is arranged to enable updating of detected phase and frequency at each clock pulse n of the processing rate $f_s$. Furthermore, the signal supply device may include a first intermediate storing member, which is provided before the adaptive filter and arranged to receive the first signal x(n) and generate a first vector X(n) including the latest first signals x(n, n−1, . . . , n−L+1), and a second intermediate storing member, which is provided for the calculating member and arranged to receive said second signals $x'_{km}(n)$ and to generate a set of second vectors X'(n) including the latest of said second signals $x'_{km}(n, n-1, \ldots, n-L+1)$.

According to a further advantageous embodiment of the invention, said space is formed by the compartment space in a vehicle. Thereby, the compartment space may include a ceiling, wherein substantially all of said sound sensors are provided in an integrated manner at the ceiling.

BRIEF DESCRIPTION OF THE DRAWINGS

The present invention is now to be described more closely by a description of an embodiment and with reference to the drawings attached, in which FIG. 1 discloses schematically a vehicle having a device according to the invention and FIG. 2 discloses schematically the construction of a device according the invention.

DETAILED DESCRIPTION OF AN EMBODIMENT OF THE INVENTION

Figure 1:
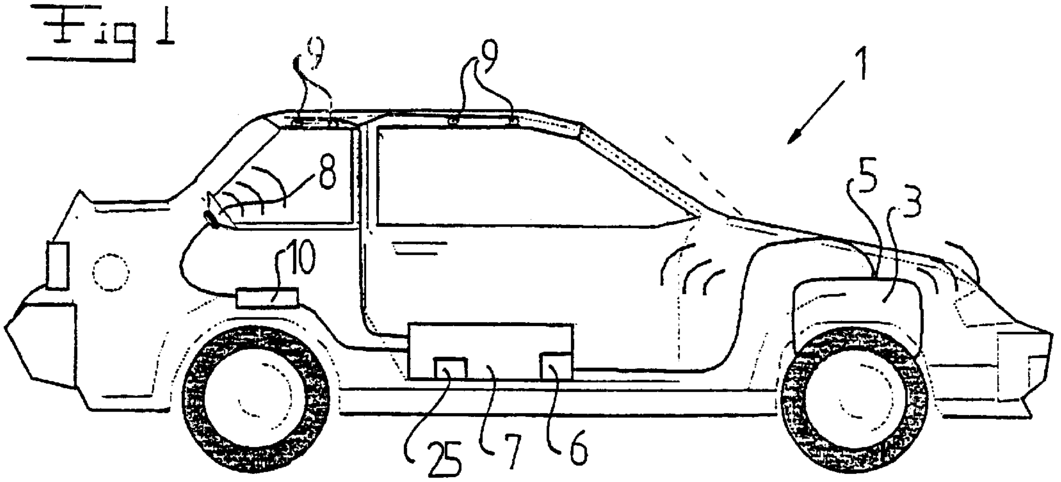
Figure 2:
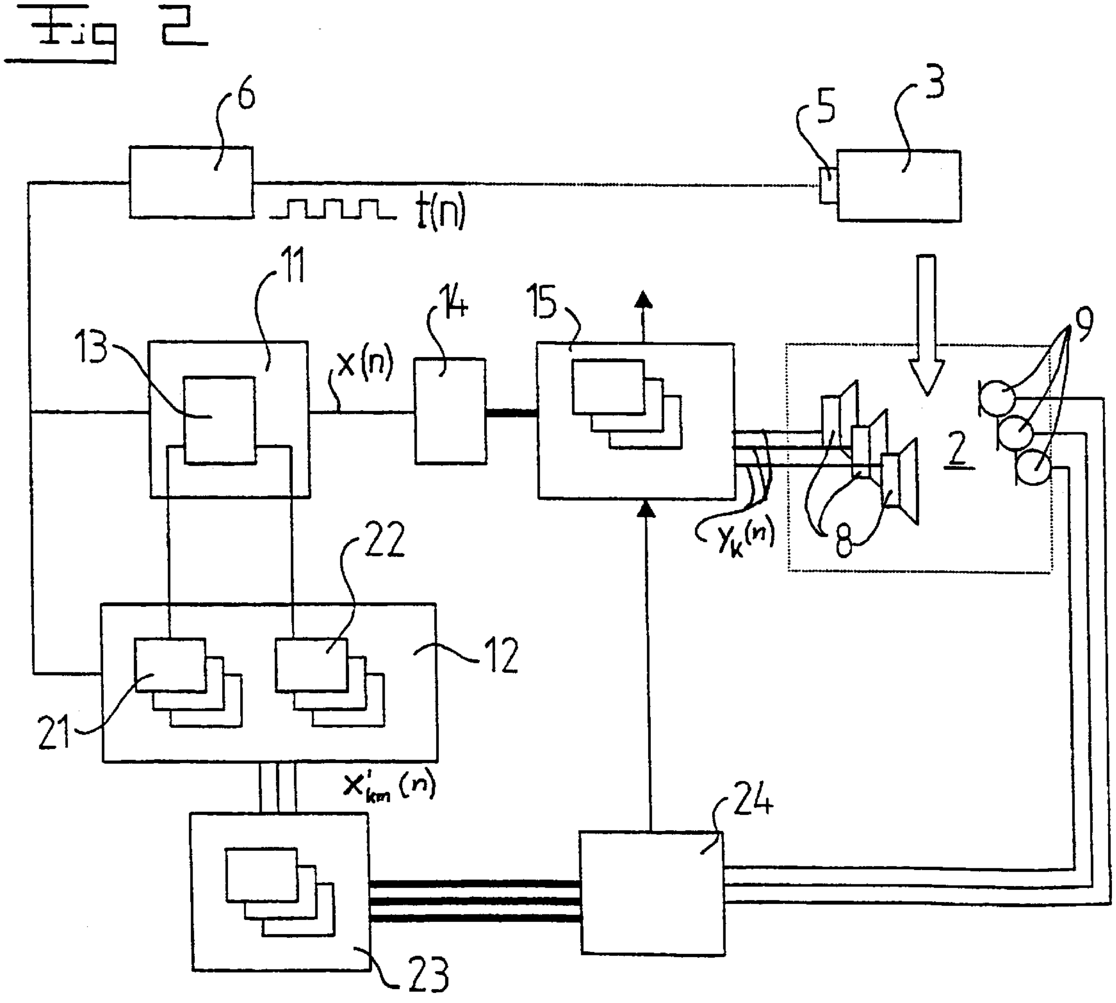

FIG. 1 discloses a vehicle 1, which defines an inner space 2 in the form of a vehicle compartment. The vehicle 1 includes an engine 3, which drives the vehicle in a conventional manner via a power transmission and driving wheels 4. During driving of the vehicle 1, sound and vibrations, which form a sound field in the inner space 2, are generated. A significant sound source of this sound field is the engine 3, and in the following a device for reducing the sound field, and in particular with regard to sound from the engine 3, is to be described.

Although it in the following example is referred to a vehicle 1, it is to be noted that invention also is applicable for reducing sounds in other connections. In particular, the device according to the invention may be used for reducing sound fields which emanate from a repeating sound source.

The device includes a pulse sensor 5, which is provided on or in the proximity of the engine 3 and arranged to sense a pulse, which is related to the fundamental frequency from the engine 3. The pulse sensor 5 thus provides a pulse signal t(n), which may have the shape of a square wave with a varying frequency. The pulse signal t(n) is supplied to a detecting member 6, which is arranged to detect phase and frequency of the pulse signal t(n). The detected phase and the detected frequency are supplied to a control unit 7 of the device. The control unit 7 is to be explained more closely below. Furthermore, the device includes a number K of sound influencing members 8, in the example disclosed in the form of loudspeakers, and a number M of sound sensors 9 in the form of microphones. The number M of microphones 9 are at least equal to the number K of loudspeakers 8. The number M of microphones may be 4–8, preferably 6. The number K of loudspeakers 8 may be 2–6, preferably 4. The loudspeakers 8 receive a drive signal $Y_k$ from the control unit 7 via an amplifier 10 and are arranged to reduce the sound field in the space 2, wherein the loudspeakers 8 interfere with or absorb the sound which is generated by the engine 3. The microphones 9 are arranged to sense the actual sound field in the space 2 and to provide an error signal $e_m(n)$ which is supplied to the control unit 7.

The control unit 7 includes a signal supply device with a first signal supply member 11 and a second signal supply member 12. The first signal supply member 11 includes a sinus table 13 and is arranged to receive detected phase and frequency of the pulse signal t(n) from the detecting member 6. Starting this phase and frequency, a sinusoidal signal is read from the approximate sinus table 13. This sinusoidal signal, which in the following is called the first signal x(n) is thus provided by the first signal supply member 11 and supplied to first intermediate storing member 14. The first intermediate storing member 14 is a so-called buffer member and is arranged to generate a first vector X(n), which includes the latest first signals x(n, n−1, . . . , n−L+1). This vector X(n) is supplied to an adaptive filter 15 of the control unit 7. The adaptive filter 15 has a number of filter coefficients $w_{km}$ and is arranged to generate, from said vector X(n), a drive signal $y_k(n)$ for each loudspeaker, wherein the drive signals $y_k(n)$ are supplied to the respective loudspeaker via the amplifier 10.

The second signal supply member 12 includes a coefficient table 21 and a precalculating member 22. The second signal supply member 12 is arranged to receive the detected phase and the detected frequency of the pulse signal t(n) from the detecting member 6 and to generate a set of second signals $x'_{km}(n)$, which are supplied to a second intermediate storing member, which is arranged to generate a set of vectors X'(n) including the latest of said second signals $x'_{km}(n, n-1, \ldots, n-L+1)$, which are supplied to a calculating member 24. The calculating member 24 also receives the error signals e(n) from the microphones 9. From the second signals $x'_{km}(n)$ and the error signals e(n), the calculating member 24 is arranged to calculate the above-mentioned filter coefficients $w_k$ of the adaptive filter 15 and to update this filter 15. The calculating member 24 operates by means of any LMS-algorithm (Least Mean Square) known per se.

The control unit 7 also includes a clock 25, which defines a processing rate $f_s$. The control unit 7 is arranged to permit said updating of the adaptive filter and to control the different calculations and updatings, which are made in the control unit by means of the processing rate $f_s$. Actual clock pulses, which are controlled by the processing rate $f_s$, is denoted n.

The coefficient table 21 includes two sets of coefficients, a first set of amplitude coefficients ρ and a second set of delay coefficients θ'. The amplitude coefficients ρ are related to the amplitude of the second signal $x'_{km}(n)$, and the delay coefficients θ' define phase relations between the pulse signal t(n) and the second signals $x'_{km}(n)$. By means of these coefficients and an approximate value, which is related to detected phase and frequency of the pulse signal t(n), preferably to the first signal x(n), said second signals $x'_{km}(n)$ may be calculated in an easy manner by means of the precalculating member 22. Said approximate value may be loaded from an approximative sinus table, which is arranged to provide this value from the delay coefficients θ' and detected phase and frequency of the pulse signal t(n). Such a sinus table may be a separate sinus table of the second signal supply member 12. However, it is also possible to utilise the sinus table 13 already present in the first signal supply member 11.

The control unit 7 may be realised by means of a computer device including at least one processor with associated memory members. Although the different included components which have been described above have been defined as members, it is to be noted that these can be realised as software of said computer.

As appears from FIG. 1, the microphones 9 are provided in the ceiling 30 of the compartment space 2. Advantageously, the microphones 9 are mounted at the ceiling 13 in such a way that they form an integrated structure with the ceiling 30. In such a way, the microphones 9 may in an easy manner be hidden. The loudspeakers 8 and the amplifier 10 may be realised by means of the music device which normally is present in modern vehicles. The device thus does not require any additional arrangements, except for a suitable device for adapting and feeding of the drive signal to the amplifier 10, but the normally four loudspeakers 8 included in such a music device ought to be sufficient.

The invention is no limited to the embodiment disclosed but may be varied and modified within the scope of the following claims.

What is claimed is:

1. A device for active sound control in a space (2) with a sound field from at least one sound source (3), comprising at least one pulse sensor (5), which is arranged to provide a pulse signal (t(n)) having a frequency which varies with a state of operation of said sound source, a detecting member (6), which is arranged to detect the phase and the frequency of said pulse signal (t(n)), a number (K) of sound influencing members (8), which are arranged to reduce the sound field in said space, a number (M) of sound sensors (9), which each is arranged to sense the actual sound field in said space (2) and provide an error signal $e_m(n)$, and a control unit (7), which includes a signal supply device (11, 12), which is arranged to receive the pulse signal (t(n)) and supply a first signal (x(n)) to an adaptive filter (15) of the control unit (7), which has a number of filter coefficients ($w_k$) and is arranged to generate, from the first signal (x(n)), a drive signal ($y_{km}(n)$) for each sound influencing member (8), and a set of second signals ($x'_{km}(n)$) to a calculating member (24), which is arranged to calculate an updating of said filter coefficients ($w_k$) by means of said second signals ($x'_{km}(n)$) and the error signals ($e_m(n)$) and to update the adaptive filter (15), characterised in that the signal supply device (11, 12) includes at least one coefficient table (21), which is arranged to provide a first set of amplitude coefficients (ρ) and a second set of delay coefficients (θ') for generating said second signals ($x'_{km}(n)$) from detected phase and frequency of the pulse signal (t(n)), wherein said first set of amplitude coefficients (ρ) are related to the amplitudes (ρ) of said second signals ($x'_{km}(n)$) and said second delay coefficients (θ') define phase relations between the pulse signal (t(n)) and said second signals ($x'_{km}(n)$).

2. A device according to claim 1, characterised in that the signal supply device includes a first signal supply member (11), which is arranged to receive detected phase and frequency of the pulse signal (t(n)) and supply said first signal (x(n)) to the adaptive filter (15), and a second signal supply member (12), which is arranged to receive detected phase and frequency of the pulse signal (t(n)) and supply said second signals ($x'_{km}(n)$) to the calculating member (24).

3. A device according to claim 2, characterised in that the second signal supply member (12) includes said coefficient table (21) and a precalculating member (22), which is arranged to calculate said second signals ($x'_{km}(n)$) by means of said first set of coefficients and an approximate value which is related to detected phase and frequency of the pulse signal (t(n)).

4. A device according to claim 3, characterised in that the approximate value is related to the first signal (x(n)).

5. A device according to claim 3, characterised in that the signal supply device (11, 12) includes at least an approximate sinus table (13), which is arranged to provide said approximate value from said second set of coefficients and detected phase and frequency of the pulse signal (t(n)).

6. A device according to claim 2, characterised in that the first signal supply member (11) includes at least one table (13), which is arranged to provide the first signal (x(n)) from detected phase and frequency of the pulse signal (t(n)).

7. A device according to claim 6, characterised in that said table of the first signal supply member (11) includes said approximate sinus table (13).

8. A device according to claim 1, characterised in that the control unit (7) includes a clock (25), which defines a processing rate ($f_s$), wherein the control unit (7) is arranged to enable updating of detected phase and frequency.

9. A device according to claim 8, characterised in that the signal supply device (11, 12) includes a first intermediate storing member (14), which is provided before the adaptive filter (15) and arranged to receive the first signal (x(n)) and to generate a first vector (X(n)) including the latest first signals (x(n, n−1, . . . , n−L+1)).

10. A device according to claim 8, characterised in that the signal supply device (11, 12) includes a second intermediate storing member (23), which is provided before the calculating member (24) and arranged to receive said second signals ($x'_{km}(n)$) and to generate a set of second vectors ($X'_{km}(n)$) including the latest of said second signals ($x'_{km}$(n, n−1, . . . , n−L+1)).

11. A device according to claim 1, characterised in that the number (M) of sound sensors (9) are at least equal to the number (K) of sound influencing members (8).

12. A device according to claim 1, characterised in that said space (2) is formed by the compartment space of a vehicle (1).

13. A device according to claim 12, characterised in that the compartment space (2) includes a ceiling, wherein essentially all of said sound sensors (9) are provided in an integrated manner at the ceiling.

* * * * *